United States Patent [19]

Herzberg et al.

[11] Patent Number: 4,549,011
[45] Date of Patent: Oct. 22, 1985

[54] MODIFIED SHEET OF MATERIAL AND METHOD OF MAKING AND USING SAME IN CONNECTION WITH BIOCHEMICAL PROCEDURES

[75] Inventors: Max Herzberg, Moshav Sataria; Falk Fish, Tel Aviv, both of Israel

[73] Assignee: Orgenics Ltd., Yavne, Israel

[21] Appl. No.: 533,770

[22] Filed: Sep. 19, 1983

[51] Int. Cl.$^4$ .................. C08L 1/02; A61F 13/00
[52] U.S. Cl. .................. 536/31; 210/500.1; 210/502.1; 424/27; 424/32; 424/81; 426/3; 426/534; 536/43; 514/8; 514/54; 514/2; 514/781; 435/179
[58] Field of Search ............ 536/31, 43; 424/81, 424/180, 362, 27, 32; 426/3, 534; 210/500.1, 502.1, 506

[56] References Cited

U.S. PATENT DOCUMENTS

| | | | |
|---|---|---|---|
| 2,798,850 | 7/1957 | Voigtman et al. | 210/502.1 |
| 2,955,067 | 10/1960 | McBurney et al. | 210/502.1 |
| 3,742,946 | 7/1973 | Grossman | 210/502.1 |
| 3,813,236 | 5/1974 | Allan | 424/362 |
| 3,985,298 | 10/1976 | Nichols | 426/3 |
| 4,025,428 | 5/1977 | Wegmuller et al. | 210/502.1 |
| 4,087,487 | 5/1978 | Wichterle et al. | 424/81 |
| 4,107,426 | 8/1978 | Gordon | 536/82 |
| 4,178,361 | 12/1979 | Cohen et al. | 424/81 |
| 4,206,301 | 6/1980 | Yolles | 426/3 |
| 4,265,875 | 5/1981 | Byrne et al. | 424/362 |
| 4,285,983 | 8/1981 | Saldarini et al. | 426/534 |
| 4,405,324 | 9/1983 | Cruz | 424/28 |
| 4,430,229 | 2/1984 | Yamawaki et al. | 210/502.1 |
| 4,446,275 | 5/1984 | Filka et al. | |

FOREIGN PATENT DOCUMENTS

| | | | |
|---|---|---|---|
| EP85166 | 8/1983 | European Pat. Off. | 210/502.1 |
| 52-5393 | 1/1977 | Japan | 210/502.1 |
| 52-38487 | 3/1977 | Japan | 210/502.1 |
| 53-129694 | 11/1978 | Japan | 210/500.1 |

OTHER PUBLICATIONS

Chemical Abstracts, vol. 90, No. 3, Jan. 15, 1979, No. 90:18444r.

*Primary Examiner*—Ronald W. Griffin
*Attorney, Agent, or Firm*—Sandler & Greenblum

[57] ABSTRACT

A sheet for separating and retaining biological molecules. The sheet is activated with a compound for covalently binding a ligand to said sheet, and then coated with ligands having an affinity for the substance of interest. A method of using the sheet for isolating and separating substances of interest and methods for forming the sheet.

40 Claims, No Drawings

MODIFIED SHEET OF MATERIAL AND METHOD OF MAKING AND USING SAME IN CONNECTION WITH BIOCHEMICAL PROCEDURES

BACKGROUND OF THE INVENTION

1. Field of the Invention

The present invention relates to a modified sheet of material which may be used in connection with biochemical procedures, and more particularly, may be used as part of a separation technique in which substances of interest preferentially adhere onto the sheet material. The invention further relates to a method of making the sheet material and a method of using the sheet material as part of a biochemical procedure.

2. Description of Prior Art

Most biologically significant substances show a high affinity to specific ligands. For purposes of this invention, a ligand may be defined as any compound capable of recognizing another molecule. Ligands may include the substrate of an enzyme-substrate reaction; the enzyme template in more complicated processes of transcription and replication; the site of activity for biomolecules having a tissue specificity, e.g., opiates for nerve cells; the complementary sequence in the case of nucleic acids; or antibodies in the case of antigens. In some instances, high affinity is not linked to a clear function such as, for example, in the specific binding of some nuclear and cytoplasmic proteins to the poly A end eukaryotic mRNA. Such affinities have been used for identification of the presence of such complement molecules as, for instance, in the isolation of antibodies by immobilizing antigens onto an agarose column (affinity chromatography); isolation of enzymes by immobilizing their substrate onto a mesh of polysaccharides, purification of poly A-rich RNA by immobilization of oligo dT or oligo U on a cellulose column; etc. All such techniques which have allowed for the identification of the presence of such a complementarity have not, however, allowed for the separation of the substance. This separation had to be performed separately by lengthy and often tedious techniques. Prior techniques also did not allow for the rapid screening of multiple samples since each sample in, for example, affinity chromatography, had to be analyzed on a separate column, be eluted and only then processed further.

Another problem with prior techniques was that when more than one component in a mixture is an active ligand, as, for example, in multiple immunoglobulin classes for a given antigen, the mixture of immunoglobulins stayed on the column and the actual assay of the different elements must be performed in a separate experiment for each sample.

Also, in the case of monoclonal antibody isolation, where hundreds of cell stains must be screened, the process was tedious and expensive.

In the pharmaceutical area, such as, for example, with drugs having receptors at nerve cell loci, where one was attempting to locate the receptors, the number of elements present rendered the task very difficult. Thus, the technique required that the active substance and the receptors being sought were determined only by a series of lengthy separation procedures, including gel electrophoresis, etc.

In view of the cumbersome and complicated nature of prior techniques, there is a strong demand for a technique by which specific interactions could be used at the same time to identify, as well as to separate and biologically purify relevant substances.

The Prior Art highlights this very problem. Chemical Abstract 90:18444r is an abstract of an article entitled A NEW METHOD FOR THE PREPARATION OF DNA CELLULOSE, by Bragioni et al., Anal Biochem, 1978, 89(2), 616–19, which discloses the use of cellulose which has been activated by cyanuric chloride (I). The abstract states that DNA binds in satisfactory amounts to the treated cellulose. Such a system is unsatisfactory since a subsequent elution step is necessary before the separated material can be processed.

It would, therefore, be advantageous if a technique were available and could be used both for locating material of interest as well as automatically separating it and making it available for subsequent processing.

SUMMARY OF THE INVENTION

It is, therefore, an object of the invention to provide a technique and material which may be used for separating biological materials of interest in such a manner that they are readily available for subsequent processing.

This and other objects are achieved according to the invention which provides for a sheet of material which has been modified by a composition which provides for a covalent bond between a ligand and the sheet of material. A preferred composition for this purpose is cyanuric chloride, although other materials such aminothiophenol may likewise be used. The significant aspect of the sheet is precisely the fact that it is in sheet form which has been treated with cyanuric chloride, or another composition, to activate it. While cyanuric chloride treatment of cellulose is known, per se, such treatments have always been used in conjunction with cellulose powder which is packed in columns. Such techniques have suffered from the disadvantages noted above. Therefore, the fact that the material of the invention is in sheet form is of particular interest.

Of course, the invention is further directed towards the method of using the sheet material, as modified, to bind a ligand. In this method the sheet is contacted with a material containing the ligand after the sheet has been treated with cyanuric chloride or another material which may covalently bind the ligand to the sheet. Using this method, the ligand affixes onto the sheet of material and is held for subsequent use.

In a like manner, the invention extends to the method of forming the sheet which includes the steps of modifying the sheet of material by contacting the sheet with a liquid solution of cyanuric chloride, or other composition capable of covalently binding the ligand to the sheet, and then permitting the sheet of material to dry.

The sheet itself may be either cellulosic or made of a plastic material, the significant feature of the invention being that the sheet include free hydroxy groups which are reactive with the cyanuric chloride. Where a cellulosic paper is used, the sheet may be in the form of a filter or blotter paper.

The ligand is covalently bonded to the sheet by means of the cynauric chloride or other material. The substance covalently bound to the cyanuric chloride may be selected from the group of proteins, polynucleotides, polysaccharides, glycoproteins, lipoproteins, carcinogens, or compounds having a biologically relevant receptor. Compounds having such a receptor also include substances capable of affecting the central nervous system. Substances capable of affecting the central nervous system include opiates.

The sheet of treated material may be used by contacting the sheet with a liquid containing the substance of interest to be identified, for example. Alternatively, the substance of interest may be present in a gel, e.g., an agar set gel such as is commonly used in electrophoresis. By laying down the sheet or paper on the gel, the substance of interest is secured onto the covalently bound ligand on the sheet. Where working from a liquid, the sheet may be in the form of a filter or blotter paper such that liquid is moved by capillary action across the sheet while ligands of interest adhere thereto and are ready for subsequent treatment.

According to yet another embodiment of the invention the sheet may itself be applied to another sheet upon which the ligand is present.

DESCRIPTION OF PREFERRED EMBODIMENTS

The present invention provides a sheet product and a process of forming and using the sheet to take up, separate and even possibly isolate biologically significant molecules. Such a sheet finds particular application in combination with gel electrophoresis or chromatographic separation. The sheet of the invention provides a flat compact surface which is homogenous and is made of cellulosic or plastic material. Substances of interest can bind specifically to the sheet and can then be detected by way of autoradiography, enzyme immunoassay or specific staining techniques.

According to a preferred embodiment, the sheet is formed by first activating a cellulosic or plastic sheet by a reaction with cyanuric chloride in a manner which has been used by others for polysaccharides (see Anal Biochem 61 392(1974)) so as to create a dichlorotriazinyl cellulose which reacts with amino groups and with some of the hydroxy groups of polysaccharides. Ligand molecules having free amino groups or reactive hydroxy groups, or molecules which are coupled to ligands which have such groups can homogeneously bind to the surface of the sheet. The flat surface which is entirely and homogeneously coated may then be used as a blotting material to blot separated components from a gel or a thin layer or from a paper chromatography system either by free diffusion, or by electrophoretic transfer. The flat surface if the sheet may also be used for screening of microplate wells to test for the presence of specific antibodies.

The sheet or substrate may be cellulosic and may be made of conventional filter paper or any natural or synthetic sheet possessing free hydroxy groups which can react with cyanuric chloride under basic conditions.

As noted above, although cyanuric chloride is a preferred material, other materials which covalently bind ligands may also be used and clearly are included within the scope of the invention.

When using cyanuric chloride the sheets are soaked in 3M NaOH or KOH. After washing off excess bases, 5-10% cyanuric chloride solution in a 1:1 dioxane:xylene mixture is added whereby the weight relationship between cyanuric chloride and the paper is approximately 1:1. After stirring, the sheets are washed in organic solvents, and rinsed in acetic acid:dioxane:water (1:2:1w/w/w). The sheets are next washed in acetone and dried under vacuum. The sheets are contacted with a solution of the ligand for a time long enough for optimum binding under constant agitation at a convenient temperature. Once the the ligand is bound, the still-active Cl groups on the sheet are inactivated by the use of a buffer which is rich in free amino groups. The sheet is then dried and is ready for use.

EXAMPLE 1

Identification of specific antigen from a crude preparation of Newcastle virus.

A sheet of paper (15×15 cm) having a weight of 2 g. was soaked for 30-45 minutes in 3M NaOH. After permitting excess liquid to drain, the sheet was soaked in a trough containing 2 g of cyanuric chloride in 35 ml of a 1:1 dioxane:xylene mixture for two hours at room temperature under slow agitation. Excess liquid is removed and the sheet is passed for fifteen minutes each into baths containing 100 ml of dioxane, dioxane, acetic acid/dioxane/water 1:2:1 (w/w/w), acetone, acetone, and tris-glycine 0.1M.

The sheet is then dried under vacuum and placed in a trough containing 20 ml of a crude anti-Newcastle-antiserum in a proportion of 1:10 with unbuffered saline and allowed to react overnight at 4° C. The sheet was then dried and ready for use. A crude preparation of Newcastle viral particles was processed for polyacrylamide gel electrophoresis according to a technique well known in the art. After protein separation and renaturation, the gel is used for electrophoretic transfer onto the sheet. After having been contacted with the gel, the sheet is extensively washed with salt solutions and only those proteins having antigenic activity corresponding to the anti-serum anti-Newcastle activity are still bound to the sheet. The samples were then stained and compared to stained gels of the viral protein and antigens identified.

EXAMPLE 2

Identification and purification of poly A binding proteins.

The sheet is prepared as in Example 1 except that the acivated paper is soaked in 0.1 mg/ml solution of poly A. Once ready, the remaining active sites on the sheet are blocked with 0.1M tris-glycine for one hour at room temperature. A gel electrophoresis of a mixture of nuclear proteins was run and used as in example 1 to electrophoretically transfer onto the sheet. Poly A binding proteins were identified and the sheet was cut at the binding sites. After soaking in a 2M salt buffer, the sheet releases the poly A binding proteins which are bound to the poly A on the sheets.

EXAMPLE 3

Identification of SV 40 Sequences

A plasmid composed of PBR 322 containing sequences having a specific affinity for SV 40 was grown, isolated and bound to the sheet as an Example 2.

Cells which were suspected carriers of SV 40 genes were processed for either DNA or RNA isolation after having been previously isotope labeled. Either DNA or RNA extract was run onto a gel of polyacrylamid after complete deproteinization of the macromolecules. The sheet was then blotted onto the gel and only those sequences complementary to the SV 40 sequences remained on the flat surface after hybridization. These sequences were identified by radioactive labeling.

Although the invention has been described with reference to specific materials, compositions and examples, it is to be understood that the invention is not limited to the particulars disclosed and extends to all equivalents falling within the scope of the claims.

What is claimed is:

1. A sheet of material modified by cyanuric chloride.
2. The sheet as defined by claim 1 wherein said sheet is cellulosic.
3. The sheet as defined by claim 1 wherein said sheet is made of plastic material.
4. The sheet as defined by either of claims 2 or 3 with a ligand bound thereto.
5. The sheet as defind by claim 4 wherein said ligand is covalently bound to said cyanuric chloride modified sheet.
6. The sheet as defined by claim 5 wherein said ligand is selected from the group consisting of proteins, polynucleotides, polysaccharides, glycoproteins, lipoproteins, carcinogens, or compounds having a biologically relevant receptor.
7. The sheet as defined by claim 6 wherein said compound having a biologically relevant receptor is selected from the group consisting of substances capable of affecting the central nervous system.
8. The sheet as defined by claim 7 wherein said substances capable of affecting the central nervous system are opiates.
9. The sheet as defined by claim 1 wherein said sheet comprises free hydroxy groups which are reactive with said cyanuric chloride.
10. The sheet as defined by claim 1 wherein said sheet is a filter paper.
11. The sheet as defined by claim 1 wherein said sheet is a blotter paper.
12. A method of binding a substance of interest comprising the step of contacting a sheet of material modified by cyanuric chloride having a ligand of said substance of interest bound thereto with said substance of interest to affix said substance of interest onto said sheet of material.
13. The method as defined by claim 12 wherein said sheet of material is cellulosic.
14. The method as defined by claim 12 wherein said sheet is made of plastic material.
15. The method as defined by either of claims 13 or 14 wherein said ligand is selected from the group consisting of proteins, polynucleotides, polysaccharides, glycoproteins, lipoproteins, carcinogens or a compound having a biologically relevant receptor.
16. The method as defined by claim 15 wherein said ligand consists of a substance capable of affecting the central nervous system.
17. The method as defined by claim 16 wherein said ligand capable of affecting the central nervous system is an opiate.
18. The method as defined by claim 12 wherein said sheet comprises free hydroxy groups which are reactive with said cyanuric chloride.
19. The method as defined by claim 12 wherein said sheet is a filter paper.
20. The method as defined by claim 12 wherein said sheet is a blotter paper.
21. The method as defined by claim 12 further comprising contacting said sheet with said substance of interest when said substance of interest is in a gel and wherein said method comprises contacting said sheet with said gel.
22. The method as defined by claim 12 further comprising contacting said sheet with said substance of interest when said substance of interest is on a separative paper and wherein said method comprises contacting said sheet with said separative paper.
23. The method as defined by claim 12 further comprising washing said sheet with a solution to remove material not affixed to said sheet.
24. The method as defined by claim 12 further comprising staining said sheet.
25. A method of forming a modified sheet of material comprising the steps of:
    (a) modifying said sheet of material by contacting said sheet of material with a liquid solution of cyanuric chloride; and
    (b) permitting said sheet of material to dry.
26. The method as defined by claim 25 further comprising binding a ligand to said sheet of step (b).
27. The method as defined by claim 26 wherein said sheet is cellulosic.
28. The method as defined by claim 26 wherein said sheet is a plastic material.
29. The method as defined by claim 26 wherein said sheet is a filter paper.
30. The method as defined by claim 26 wherein said ligand is selected from the group consisting of: proteins, pllynucleotides, polysaccharides, glycoproteins, lipoproteins, carcinogens, or compounds having a biologically relevant receptor.
31. The method as defined by claim 30 wherein said compounds having a biologically relevant receptor are selected from the group consisting of substances capable of affecting the central nervous system.
32. The method as defined by claim 31 wherein said substances capable of affecting the central nervous system are opiates.
33. The method as defined by claim 25 wherein said sheet comprises free hydroxy groups which are reactive with said cyanuric chloride.
34. The method as defined by claim 25 wherein said sheet is a filter paper.
35. The method as defined by claim 25 wherein said sheet is a blotter paper.
36. A sheet of material modified by a composition capble of covalently binding a ligand.
37. A method of binding a substance of interest to a sheet of material comprising the steps of:
    (a) contacting the sheet of material with a composition capable of covalently binding a ligand to said sheet;
    (b) contacting said sheet with a ligand solution to bind said ligand thereto;
    (c) contacting said sheet having said ligand bound thereto with said substance of interest to bind said substance thereto.
38. The method as defined by claim 37 further comprising washing said sheet with a solution to remove material not affixed to said sheet.
39. The method as defined by claim 37 further comprising staining said sheet.
40. A method of forming a modified sheet of material comprising the steps of:
    (a) modifying said sheet of material by contacting said sheet of material with a liquid solution of a composition capable of covalently binding a liquid to said sheet; and
    (b) permitting said sheet of material to dry.

* * * * *